(12) United States Patent
Nilson et al.

(10) Patent No.: US 7,589,786 B2
(45) Date of Patent: Sep. 15, 2009

(54) MULTI-VIEW IMAGING OF A SAMPLE IN A BOX

(75) Inventors: David Nilson, Walnut Creek, CA (US); Michael D. Cable, Danville, CA (US); Bradley W. Rice, Danville, CA (US)

(73) Assignee: Xenogen Corporation, Alameda, CA (US)

( * ) Notice: Subject to any disclaimer, the term of this patent is extended or adjusted under 35 U.S.C. 154(b) by 456 days.

(21) Appl. No.: 11/486,239

(22) Filed: Jul. 12, 2006

(65) Prior Publication Data

US 2006/0250518 A1    Nov. 9, 2006

(51) Int. Cl.
*H04N 5/225* (2006.01)
*A61B 5/06* (2006.01)
(52) U.S. Cl. ...................... 348/373; 600/407
(58) Field of Classification Search ......... 348/373–376; 600/407, 477; 359/384, 391–398
See application file for complete search history.

(56) References Cited

U.S. PATENT DOCUMENTS

| | | | |
|---|---|---|---|
| 4,819,660 A * | 4/1989 | Smith ........................ 600/587 |
| 5,202,091 A | 4/1993 | Lisenbee |
| 5,319,209 A | 6/1994 | Miyakawa et al. |
| 5,414,258 A | 5/1995 | Liang |
| 5,598,453 A * | 1/1997 | Baba et al. .................. 378/146 |
| 5,636,299 A | 6/1997 | Bueno et al. |
| 5,637,874 A | 6/1997 | Honzawa et al. |
| 5,650,135 A | 7/1997 | Contag et al. |
| 5,672,881 A | 9/1997 | Striepeke et al. |
| 5,705,807 A | 1/1998 | Throngnumchai et al. |
| 5,738,101 A | 4/1998 | Sappey |
| 5,812,310 A | 9/1998 | Stewart et al. |
| 5,840,572 A | 11/1998 | Copeland et al. |
| 5,867,250 A | 2/1999 | Baron |
| 5,970,164 A | 10/1999 | Bamberger et al. |
| 6,217,847 B1 | 4/2001 | Contag et al. |
| 6,242,743 B1 | 6/2001 | DeVito et al. |
| 6,321,111 B1 | 11/2001 | Perelman et al. |
| 6,364,829 B1 | 4/2002 | Fulghum |
| 6,414,713 B1 * | 7/2002 | Ebisawa et al. ............. 348/131 |
| 6,615,063 B1 | 9/2003 | Ntziachristos et al. |

(Continued)

FOREIGN PATENT DOCUMENTS

JP    2001-161696    6/2001

(Continued)

OTHER PUBLICATIONS

International Search Report dated Oct. 28, 2002 in PCT Application No. PCT/US02/22162.

(Continued)

*Primary Examiner*—Timothy J Henn
(74) *Attorney, Agent, or Firm*—Beyer Law Group LLP

(57) ABSTRACT

Systems and methods are provided for taking images of a sample. The sample is placed in an imaging box comprising a moveable stage that allows images of the sample to be taken from various positions and angles within the imaging box. The images are taken by a camera and sent to a processor. Structured light images obtained from one or more views within the imaging box may be used to build a structured light representations of the sample.

22 Claims, 15 Drawing Sheets

U.S. PATENT DOCUMENTS

| | | | |
|---|---|---|---|
| 6,642,953 | B1 | 11/2003 | Nieto Velasco et al. |
| 6,646,678 | B1 | 11/2003 | Kobayashi |
| 6,775,567 | B2 | 8/2004 | Cable et al. |
| 6,919,919 | B2 | 7/2005 | Nelson et al. |
| 6,963,375 | B1 | 11/2005 | Lundberg |
| 7,113,217 | B2 | 9/2006 | Nilson et al. .................. 07/13 |

FOREIGN PATENT DOCUMENTS

| | | |
|---|---|---|
| JP | 2002-520616 | 7/2002 |
| JP | 2002-535025 | 10/2002 |
| WO | WO 00/04371 | 1/2000 |
| WO | WO 00/17643 | 3/2000 |
| WO | WO 00/42910 | 7/2000 |
| WO | WO 0163247 | 8/2001 |

OTHER PUBLICATIONS

Japanese Office Action dated Jan. 22, 2008 in JP Application No. 2003-512685.

Benaron, David A., *A System for Imaging Infection and Gene Expression in the Body in 3-D*, Biomedical Optical Spectroscopy and Diagnostics, 1998 Technical Digest, © 1998 Optical Society of America, pp. 134-135.

Takeda, Mitsuo; Ina, Hideki; and Kobayashi, Seiji, *Fourier-transform method of fringe-pattern analysis for computer-based topography and interferometry*, J. Opt. Soc., Am., vol. 72, No. 1, Jan. 1982, pp. 156-160.

Toyooka, Satoru and Iwaasa, Yuuji, *Automatic profilometry of 3-D diffuse objects by spatial phase detection*, Applied Optics, vol. 25, No. 10, May 15, 1986, pp. 1630-1633.

Mahmood et al., "Near Infrared Optical Imaging of Protease Activity for Tumor Detection", Radiology, Dec. 1999, p. 866-870.

Office Action dated Nov. 26, 2008 in U.S. Appl. No. 11/485,721.

Japanese Office Action dated Jan. 6, 2009 in JP Application No. 2003-512685.

Office Action dated Jun. 15, 2009 in European Application No. 02746997.2.

Notice of Allowance dated Jul. 1, 2009 in US Appl. No. 11/485,721.

Office Action dated Apr. 28, 2009 in US Appl. No. 11/485,721.

\* cited by examiner

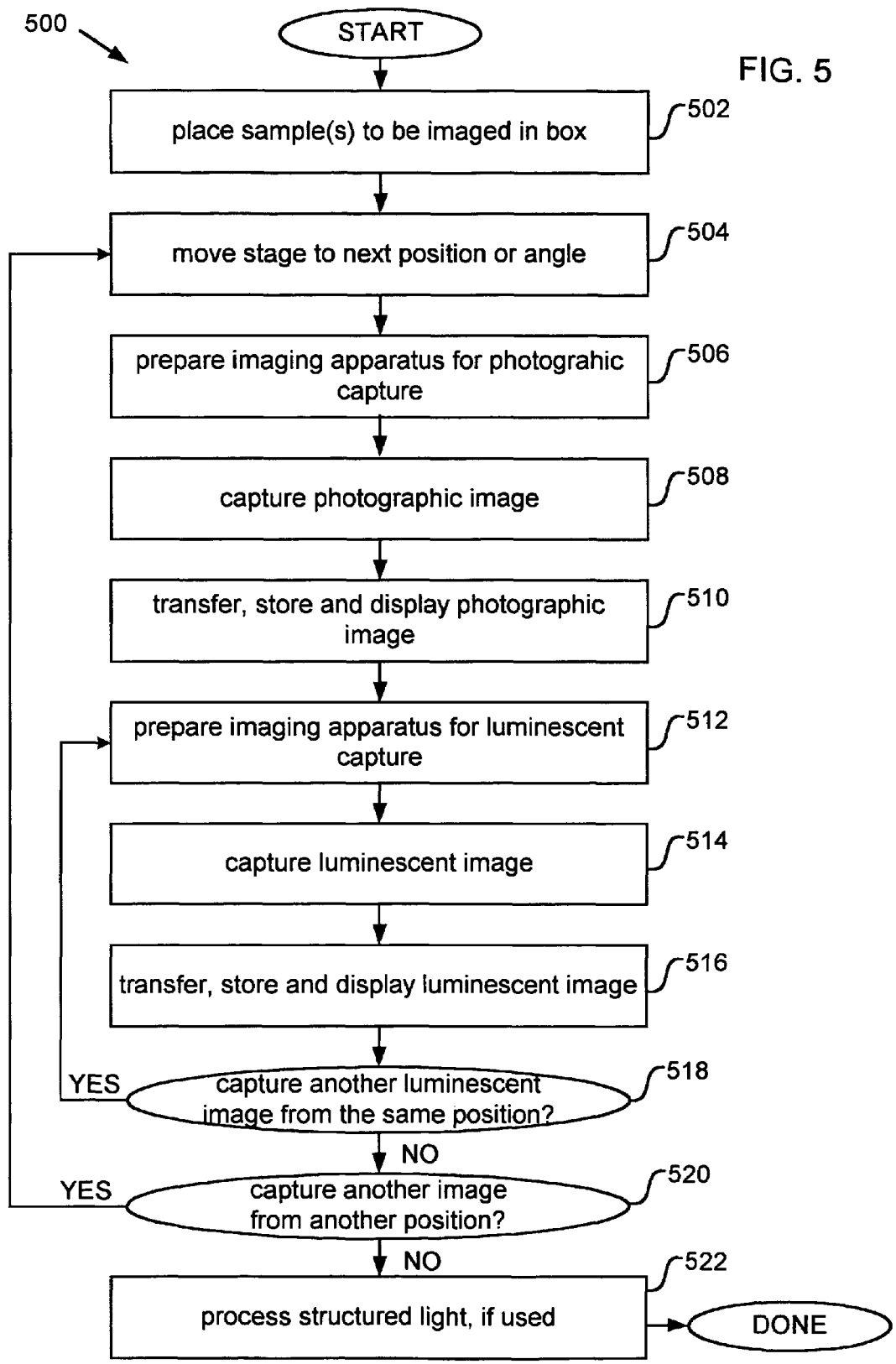

MULTI-VIEW IMAGING OF A SAMPLE IN A BOX

CROSS-REFERENCE TO RELATED APPLICATIONS

This application claims priority under U.S.C. §120 from U.S. patent application Ser. No. 09/905,668, filed Jul. 13, 2001 now U.S. Pat. No. 7,113,217 and entitled, "MULTI-VIEW IMAGING APPARATUS", which is incorporated herein for all purposes.

FIELD OF THE INVENTION

The present invention relates generally to imaging systems and their methods of use. More specifically, the present invention relates to imaging systems and methods used in capturing images from multiple views.

BACKGROUND OF THE INVENTION

One specialized type of imaging involves the capture of low intensity light (on the order of individual photons) from a light emitting sample, and the construction of images based on the photon emission data. This source of light in the sample visually indicates the origin of the activity of interest. For example, specialized in-vivo imaging applications may include analysis of one or more representations of photon emissions from internal portions of a specimen superimposed on a photographic representation of the specimen. The luminescence representation indicates portions of the specimen where an activity of interest may be taking place. The photographic representation provides the user with a pictorial reference of the specimen.

In-vivo imaging is performed by capturing an image of the sample using a camera. Intensified or cooled charge-coupled device (CCD) cameras are often used to detect the localization of low intensity light-producing cells in the sample. These cameras are considerably complex, require specialized cooling, and are fixed to a single location on the top of a specimen chamber. A user places a sample at a predetermined position on the bottom of the specimen chamber within the field of view for the overhead camera. This static relationship between camera and sample limits image capture to overhead images only.

Often, it is desirable to capture different views of the sample. For example, the detection of internal light-producing cells from the underside of a mammalian sample may be affected by covering tissue which the light must penetrate before being captured by the overhead camera. By gathering data from different angles, a user can obtain more information about the location and intensity of a light source in the animal than possible using only a single view. However, it may be impractical to reposition the sample to capture a different view when using an overhead camera.

In view of the foregoing, an improved imaging system that enables the capture of images from different views without repositioning the posture of the sample would be highly desirable.

SUMMARY OF THE INVENTION

The present invention relates to systems and methods for capturing an image of a sample. The sample is placed on a moveable stage in an imaging box. The moveable stage allows an image of the sample, or portions thereof, to be captured by a camera from different views, angles, and positions within the imaging box without repositioning the posture of the sample. As the sample is variably located within the imaging box, a light transmission device assists image capture by transmitting light emitted or reflected from the sample to a common datum associated with a camera.

In one aspect, the present invention includes a processor which is electrically coupled to the camera. The processor may also provide control of the moveable stage. In one embodiment, a transparent stage is used to allow image capture from angles beneath the stage.

In another configuration, the imaging system comprises an imaging box having a set of walls enclosing an interior cavity. The imaging system also includes a camera mount configured to position the camera relative to a fixed datum on one of the walls for viewing by the camera and a light transmission device. The imaging system additionally comprises a moveable stage apparatus including a transport mechanism and a stage configured to support the sample within the interior cavity. The stage is coupled to the transport mechanism for movement of the sample to one of a plurality of positions in the interior cavity. The transport mechanism and the light transmission device cooperate to direct light reflected or emitted from the sample to the fixed datum to capture the image by the camera.

In another aspect, the imaging apparatus comprises an imaging box including an interior cavity for receiving the sample and a stage for supporting the sample. The imaging apparatus further comprises a first linear actuator attached to the imaging box and capable of positioning the moveable stage in a first direction. The imaging apparatus additionally comprises a second linear actuator attached to the first linear actuator, attached to the stage, and capable of positioning the moveable stage in a second direction. The first linear actuator and the second linear actuator cooperate to position the stage at one of a plurality of positions in the interior cavity.

In yet another aspect, the imaging apparatus includes a positioning arm rotably coupled to the stage and rotably coupled to the imaging box such that the stage remains substantially horizontal for any rotational position of the positioning arm relative the imaging box. The imaging apparatus additionally includes a mirror attached to positioning arm. The mirror is configured to reflect light emitted from the sample at least partially along a fixed datum.

In another aspect, the invention relates to a method for imaging a sample. The sample is supported by a stage moveable within an imaging box that is coupled to a camera configured to capture an image of the sample. The method includes moving the stage to a first position in the imaging box. The method also includes capturing a first image of the sample from the first position using the camera. The method further includes moving the stage to a second position in the imaging box. The second position has a different angle relative to a fixed datum associated with the camera than the first position. The method additionally includes capturing a second image of the sample from the second position using the camera.

In still another aspect, the invention relates to a stage apparatus for use with an imaging system for capturing an image of a sample with a camera. The imaging system includes an imaging box having a set of walls defining an interior cavity, and a camera mounted relative to a fixed datum on one of the walls. The stage apparatus comprises a light transmission device, and a transport mechanism. The stage apparatus further includes a stage configured to support the sample within the interior cavity where the stage is coupled to the transport mechanism for movement of the sample to one of a plurality of positions in the interior cavity. The transport mechanism and the light transmission device cooperate to direct light reflected or emitted from the sample on the stage to the fixed datum to capture the image by the camera.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which:

FIG. 5 is a process flow illustrating a method of capturing photographic and luminescence images using the imaging apparatus of FIG. 1A in accordance with one embodiment of the present invention.

DETAILED DESCRIPTION

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, procedures, components, and circuits have not been described in detail so as not to unnecessarily obscure aspects of the present invention.

I. Imaging System

Figure 1A:
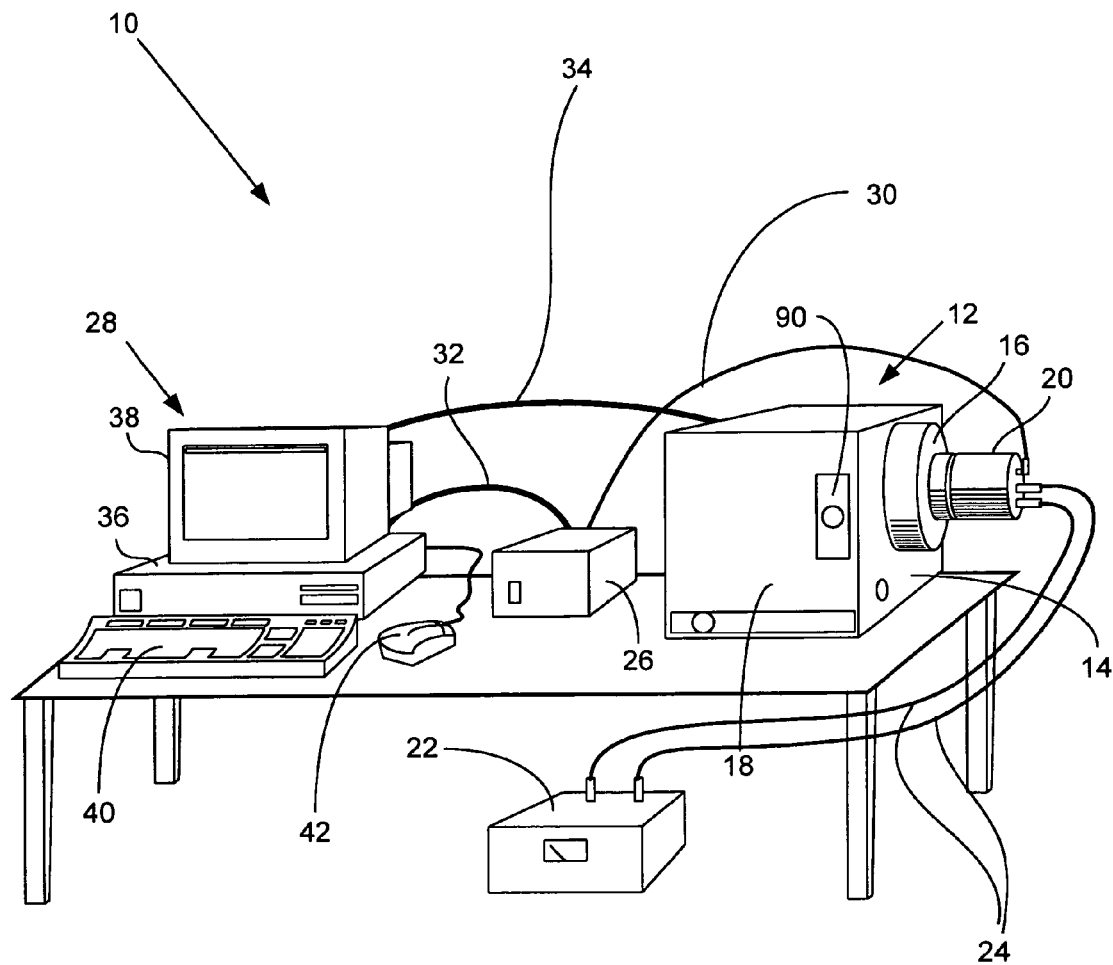
FIG. 1A is a perspective view of an imaging system including an imaging box adapted to capture images in accordance with one embodiment of the invention.

In one aspect, the present invention relates generally to improved imaging systems. FIG. 1A illustrates an imaging system 10 adapted to capture photographic and luminescence images in accordance with one embodiment of the present invention. The system 10 provides user automated control of image capture in an imaging box 12. The imaging system 10 is also useful for capturing and constructing structured light images.

The imaging system 10 comprises an imaging box 12 adapted to receive a light-emitting sample in which low intensity light, e.g., luciferase-based luminescence, is to be detected. The imaging box 12 includes a housing 16 on a side vertical wall of the box having a camera mount 109 (FIGS. 2A-2C) adapted to receive a camera. The imaging box 12 is configured to be "light-tight", i.e., essentially all external light is prevented from entering the box 12 from the ambient room.

A high sensitivity camera, e.g., an intensified or a charge-coupled device (CCD) camera 20, is attached to the imaging box 12 preferably through the camera mount 109 affixed to the housing 16. The CCD camera 20 is capable of capturing luminescent and photographic (i.e., reflection based images) images of the sample within the imaging box 12. The CCD camera 20 may optionally be cooled by a suitable source such as a refrigeration device 22 that cycles a cryogenic fluid through the CCD camera via conduits 24. A suitable refrigeration device is the "CRYOTIGER®" compressor, which can be obtained from IGC-APD Cryogenics Inc., Allentown, Pa. Other refrigerants, such as liquid nitrogen or solid state devices, may be used to cool the CCD camera 20.

An image processing unit 26 optionally interfaces between camera 20 and a computer 28 through cables 30 and 32, respectively. The computer 28, which may be of any suitable type, typically comprises a main unit 36 that contains hardware including a processor, memory components such as random-access memory (RAM) and read-only memory (ROM), and disk drive components (e.g., hard drive, CD, floppy drive, etc.). The computer 28 also includes a display 38 and input devices such as a keyboard 40 and mouse 42. The computer 28 is in communication with various components in the imaging box 12 via cable 34.

To provide communication and control for these components, the computer 28 includes suitable processing hardware and software configured to provide output for controlling any of the devices in the imaging box 12. The processing hardware and software may include an I/O card, control logic for controlling any of the components of the imaging system 10, and a suitable graphical user interface for the imaging system 10. The computer 28 also includes suitable processing hardware and software for the camera 20 such as additional imaging hardware, software, and image processing logic for processing information obtained by the camera 20. Components controlled by the computer 28 may include the camera 20, the motors responsible for camera 20 focus, one or more motors responsible for position control of a stage supporting the sample, the camera lens, f-stop, etc. The logic in computer 28 may take the form of software, hardware or a combination thereof. The computer 28 also communicates with a display 38 for presenting imaging information to the user. By way of example, the display 38 may be a monitor, which presents an image measurement graphical user interface (GUI) that allows the user to view imaging results and also acts an interface to control the imaging system 10.

The processing hardware and software may also include a suitable processor configured to provide control signals to a motor coupled to a moveable stage included in box 12. The processor may also be configured to prevent the stage from contacting the light transmission device during movement of the stage. In addition to control functions, the processor may also be applied to perform various image processing functions described herein. For example, the processor may be configured to produce a structured light representations using 2-D structured light images taken from one or more positions of the stage in the interior cavity.

The imaging system 10 is suitable for capturing images from a variety of views and positions of the sample relative to the camera 20. These images may be used in in-vivo imaging applications that include analysis of one or more representations of emissions from internal portions of a specimen superimposed on a photographic representation of the specimen. In one embodiment, the imaging system 10 is used for 2-D and structured light imaging of a low intensity light source, such as luminescence from luciferase-expressing cells, fluorescence from fluorescing molecules, and the like. The low intensity light source may be emitted from any of a variety of light-emitting objects or samples which may include, for example, tissue culture plates, multi-well plates (including 96, 384 and 864 well plates), and animals or plants containing light-emitting molecules, such as various mammalian subjects including mice containing luciferase expressing cells.

In one application, the sample is a biological specimen containing light producing cells. The resulting luminescence image may therefore be captured without using any light sources other than the sample itself. Luminescence from the sample is recorded as a function of position to produce the luminescence image. One approach to generating such composite photographic/luminescence images is described in U.S. Pat. No. 5,650,135 issued to Contag et al. on Jul. 22, 1997. The entire disclosure of that patent is incorporated herein by reference for all purposes.

In one particular embodiment, a 2-D luminescence image represents a collection of emitted photons received by each detector pixel of the CCD camera 20 over a defined length of time. In other words, the luminescence image may display magnitude values representing the photon counts at the individual detector pixels. Regions of the sample emitting radiation (e.g., photons) will appear in the luminescence image. The luminescence images may indicate the presence of a biocompatible entity, for example. The entity can be a molecule, macromolecule, cell, microorganism, a particle or the like. Thus, an in-vivo analysis may include detecting localization of a biocompatible entity in a mammalian subject. Alternatively, the information in the live mode may be used to track the localization of the entity over time. For more examples of analysis applications for a digital overlay image suitable for use with the present invention, the reader is referred to in U.S. Pat. No. 5,650,135, which was previously incorporated by reference.

II. Imaging Box

Figure 1B:
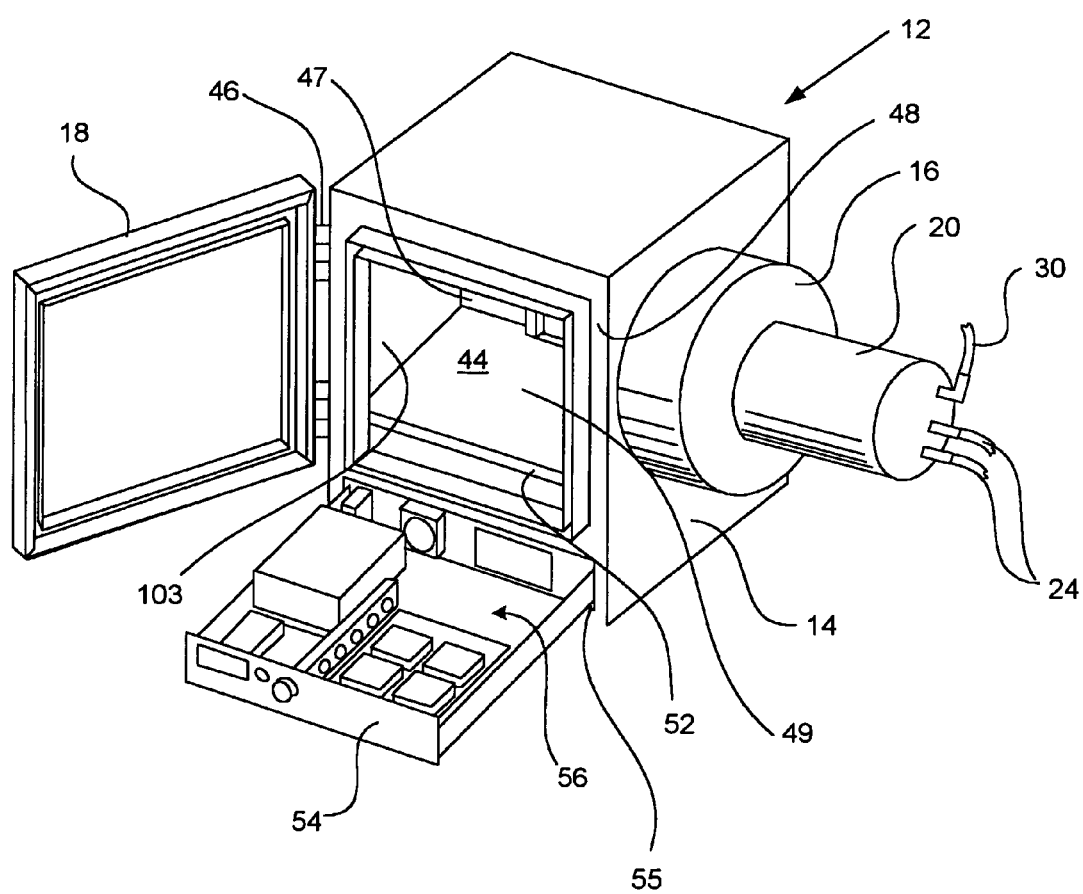
FIG. 1B illustrates the structural components of the imaging box of FIG. 1A in accordance with one embodiment of the present invention.

In one aspect, the present invention relates to an imaging apparatus suitable for various imaging operations. FIG. 1B illustrates the external components of imaging box 12 of FIG. 1A in accordance with one embodiment of the present invention. FIGS. 2A-E and 4A-D illustrate internal components of box 12 in accordance with various embodiments of the present invention. Each of the imaging apparatus described are capable of capturing an image of a sample in box 12 using a camera coupled thereto.

As shown in FIG. 1B, the imaging box 12 is illustrated with a door 18 in an open position, showing an interior cavity 44 for receiving the sample. The interior cavity 44 is defined by opposing side enclosure panels 103a and 103b (103b visible in FIG. 2D), a light-tight partition 52 on the bottom, a top panel (not shown), a back enclosure panel 47, and a front wall 48 defining a cavity opening 49 into the interior cavity 44.

Below the cavity 44 is a smaller compartment separated therefrom by the light-tight partition 52, the upper surface of which serves as a floor for the cavity 44. In one embodiment, the smaller compartment provides a housing space which is adapted to slideably receive a drawer 54 though a front opening 55 formed in the body 14. The drawer 54 houses electronic components 56 which are in electrical communication with the computer 28 (FIG. 1A) and control various components and functions of the box 14. In a specific embodiment, the imaging box 12 has a body 14 made of a suitable metal such as steel.

A latchable door 18 is pivotally attached to box body 14 by way of hinges 46 which permit the door 18 to be moved from the closed position as shown in FIG. 1A to the open position as shown in FIG. 1B. In the open position, door 18 enables user access to the cavity 44 through the opening 49. In the closed position, door 18 prevents access to the cavity interior 44 through the cavity opening 49.

Figure 2A:
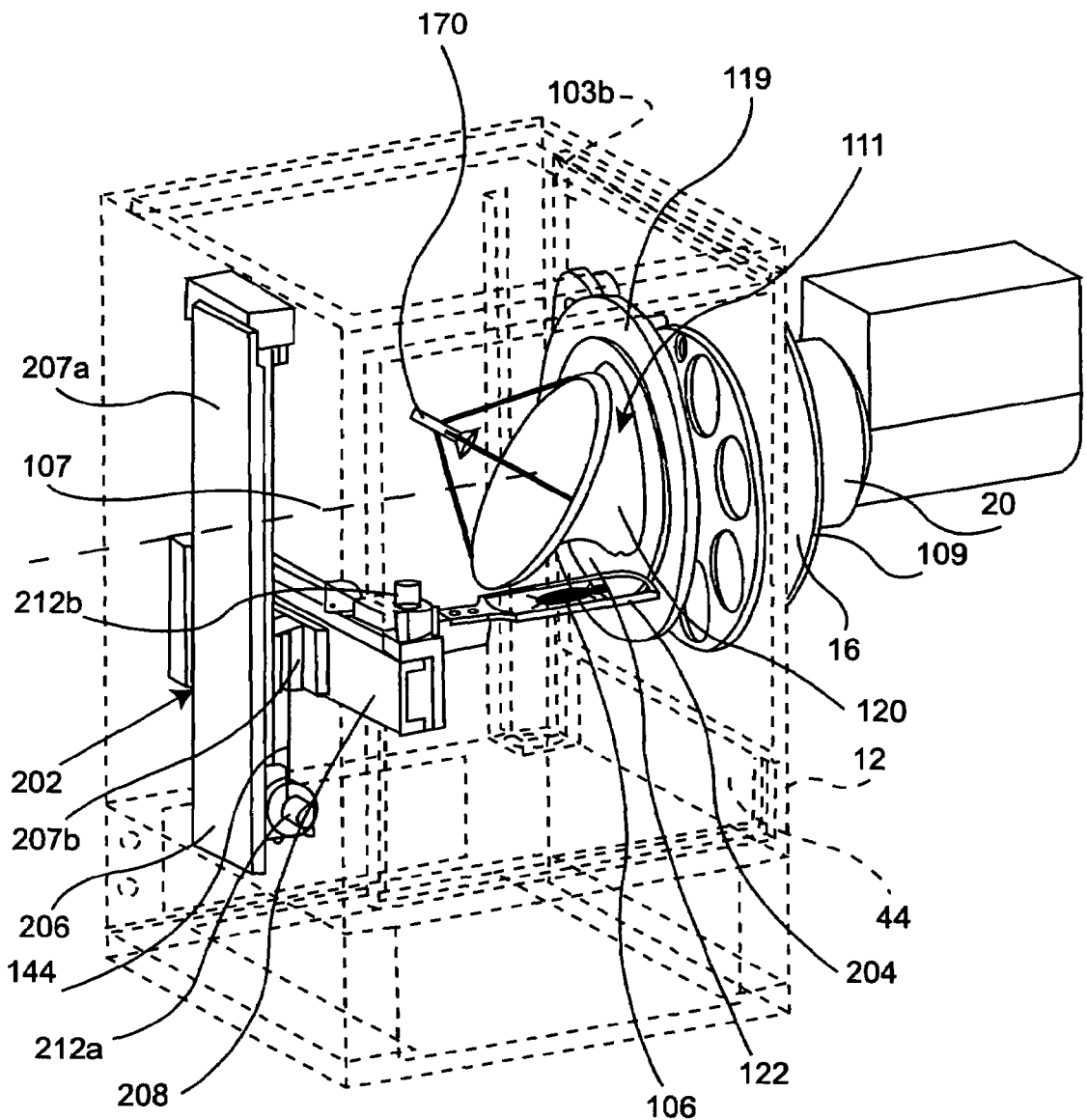
FIG. 2A illustrates a top perspective view of the components in the box of FIG. 1A with the exterior walls removed showing the moveable stage directly below a fixed datum in accordance with one embodiment of the present invention.
Figure 2B:
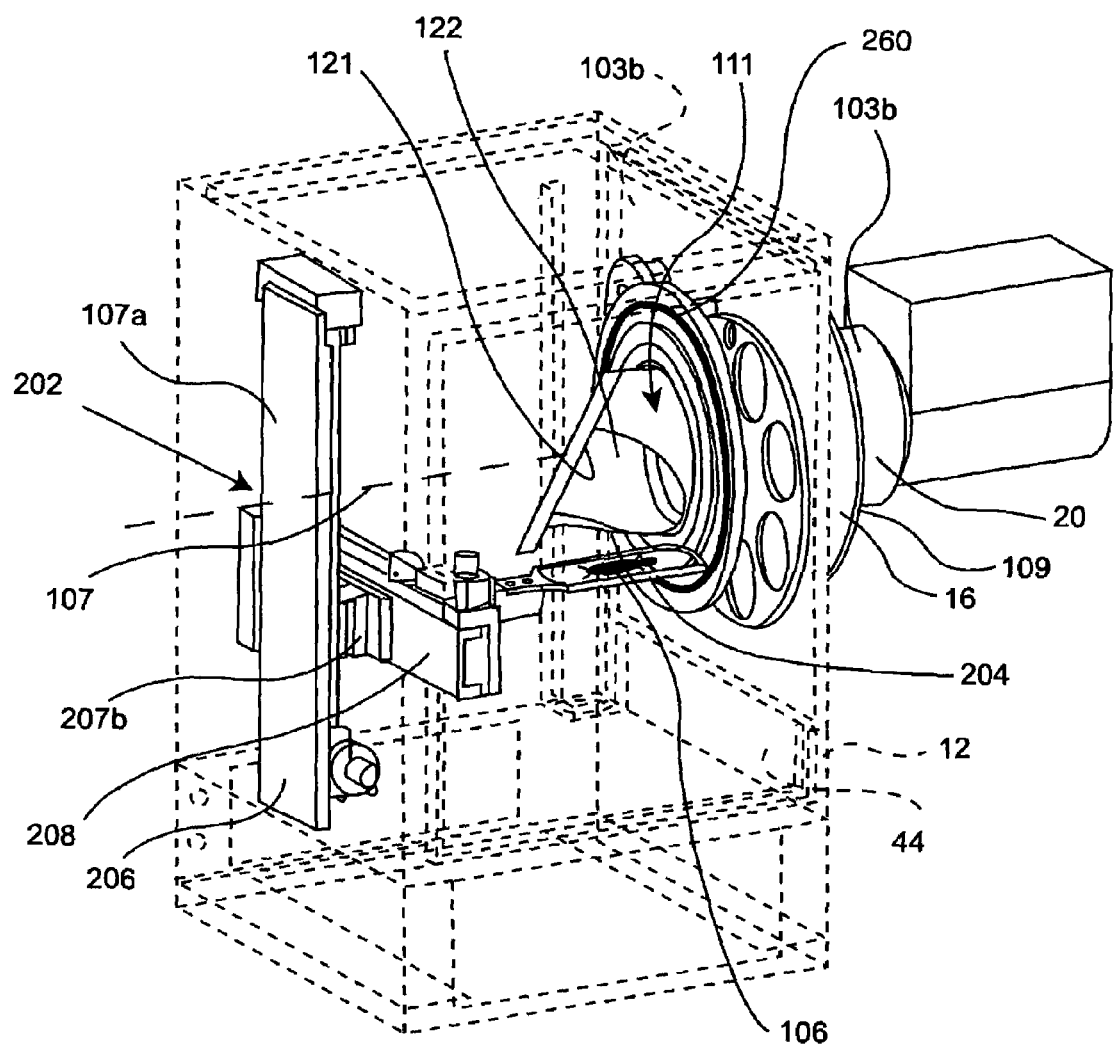
FIG. 2B illustrates a top perspective view of the components in the box of FIG. 1A with the exterior walls removed showing the moveable stage below and off-center from the fixed datum in accordance with one embodiment of the present invention.
Figure 2C:
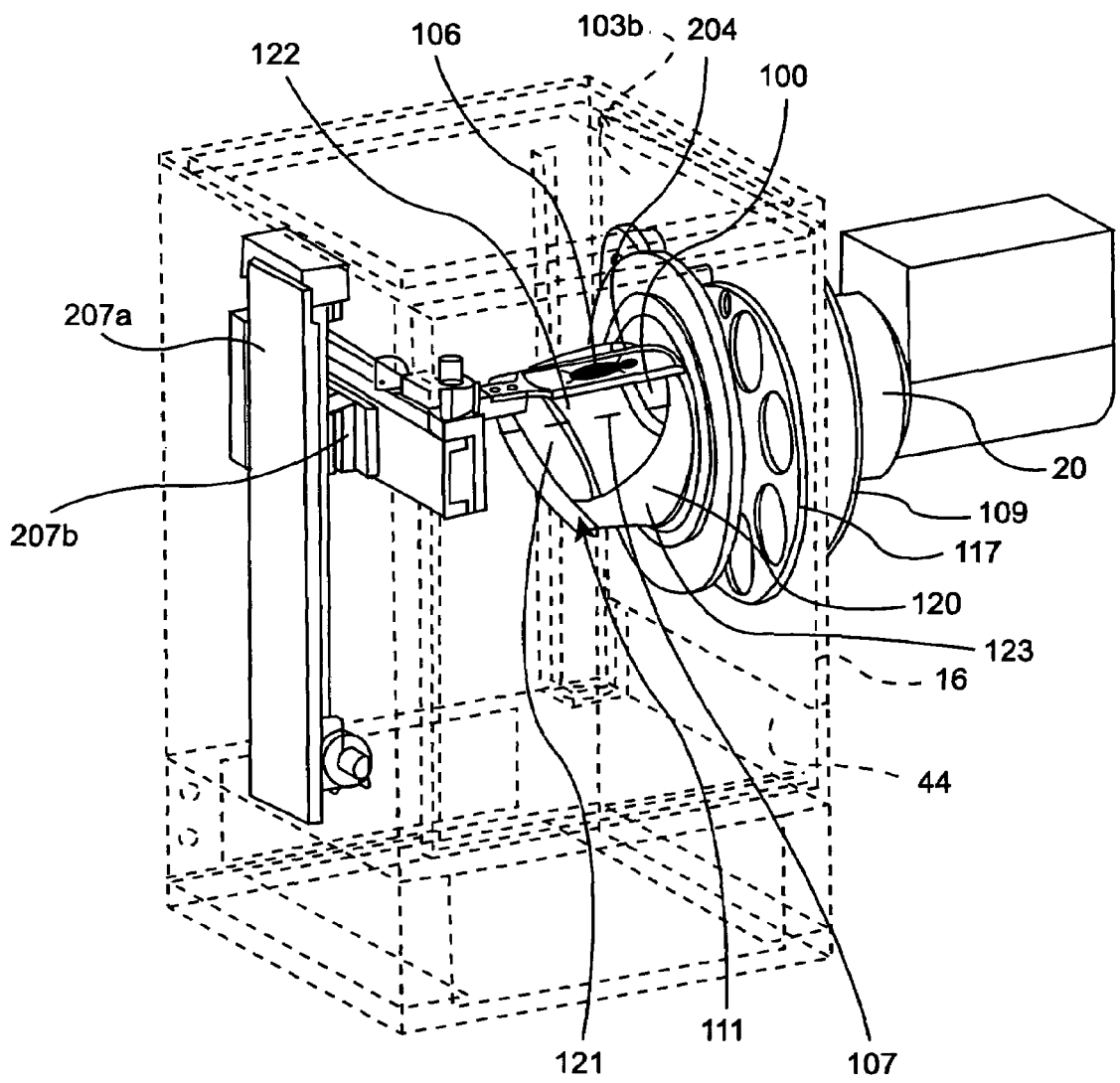
FIG. 2C illustrates a top perspective view of the components in the box of FIG. 1A with the exterior walls removed showing the moveable stage above and off center from the fixed datum in accordance with one embodiment of the present invention.
Figure 2D:
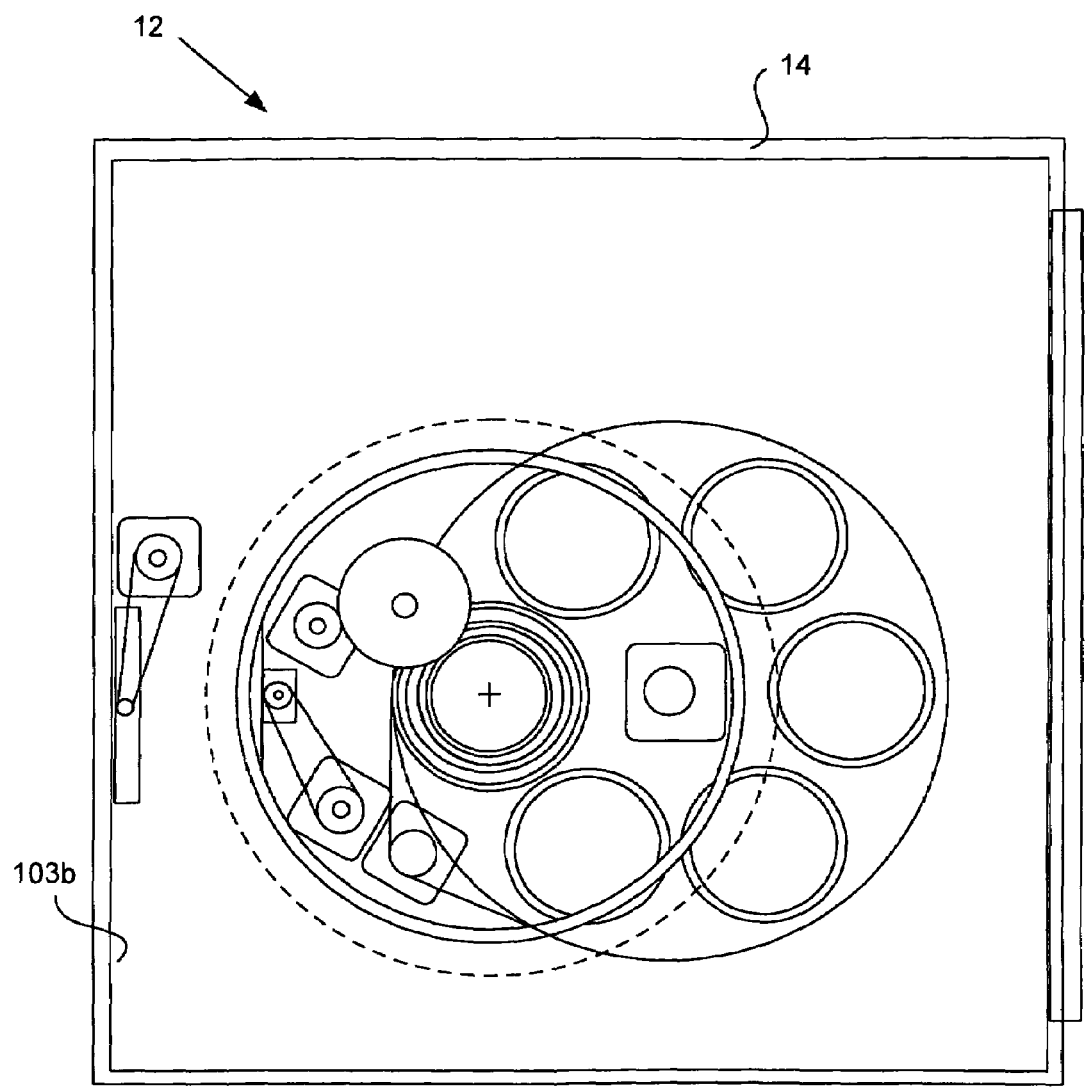
FIG. 2D illustrates an internal side view of a side wall and housing included for the box of FIG. 1A in accordance with one embodiment of the present invention.
Figure 2E:
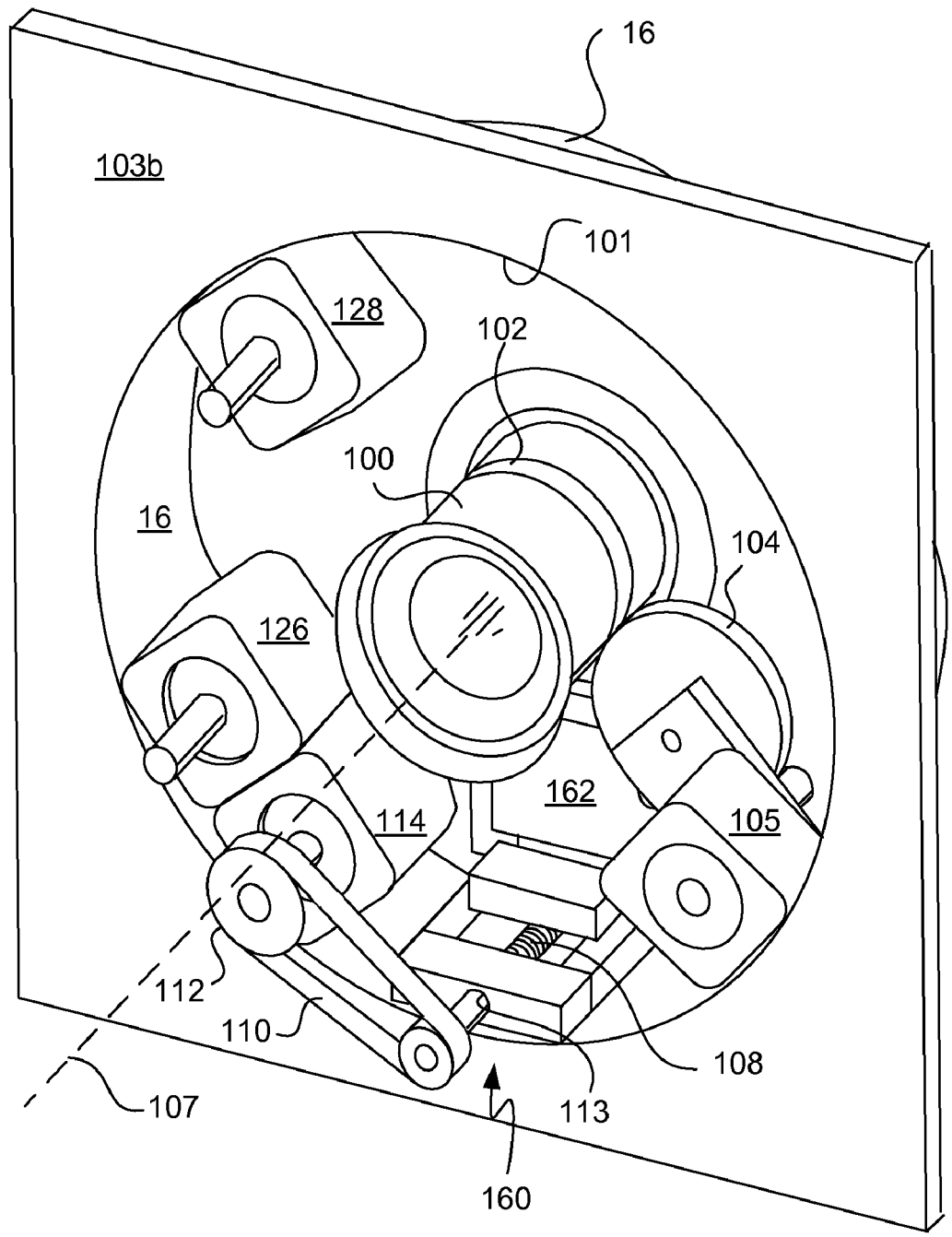
FIG. 2E illustrates an internal top perspective view of a side wall and housing for the box of FIG. 1A in accordance with one embodiment of the present invention.

Referring now primarily to FIGS. 2A-E, various internal components of box 12 (shown in broken lines) will now be described in accordance with one embodiment of the present invention. FIG. 2A is a top perspective view of the components in box 12 with the exterior walls removed showing stage 204 directly below fixed datum 107. FIG. 2B is a top perspective view of the components in box 12 with the exterior walls removed showing stage 204 below and off-center from fixed datum 107. FIG. 2C is a top perspective view of the components in box 12 with the exterior walls removed showing stage 204 above and off center from fixed datum 107. FIG. 2D is an internal side view of box 12 showing side wall 103b and housing 16 without light transmission device 111. FIG. 2E is an internal top perspective view of side wall 103b and housing 16 without light transmission device 111. FIGS. 2A-E are all shown with door 18 and exterior walls removed for illustration.

Referring to FIGS. 2C-2E, camera 20 is mounted to side housing 16 with the camera lens 100 in view of interior cavity 44 through a port 101 formed in side wall 103b of box 12. The camera lens 100 is optically coupled to camera 20 of FIG. 1A and includes a user controlled aperture or F-stop ring 102 for adjusting the F-stop or aperture of lens 100, thereby modulating the amount of light passing through the lens. A Navitar, f 0.95, 50 mm TV lens is suitable for use as camera lens 100. The F-stop ring 102 includes circumferentially disposed teeth that engage a gear 104 driven by an F-stop motor 105. The F-stop motor 105 is in electrical communication with the electrical components 56 and controlled by computer 28. Collectively, the motor 105 and a processor in computer 28 cooperate to position the f-stop of lens 100.

A focusing mechanism 160 (FIG. 2E) provides reciprocal movement of the lens for focusing thereof. The focusing mechanism includes a lens support 162 showing a stationary portion mounted to upper housing 16 and a movable portion that includes a threaded bore 113. A bolt 108, operably engageable with bore 113, includes a wheel that is driven by a toothed belt 110 through a corresponding drive wheel 112 of a camera lens focus motor 114 to move camera lens 100 into focus. The camera lens focus motor 114 is in electrical communication with the electrical components 56 and controlled by a processor included in computer 28 of FIG. 1A.

A fixed datum represents a fixed region along the line of site of the camera lens 100 into the interior cavity 44 of the box 12. Thus, the fixed datum 107 extends from the interior cavity in a direction substantially perpendicular to side wall 103*b* and through the center of camera lens 100 (FIGS. 2A-E). This datum 107, for clarity, is represented by a stationary axis that provides a reference line of site upon which the transport mechanism 202 and the light transmission device 111 cooperate therebetween to direct light reflected or emitted from sample 106 towards and into the camera lens 100 to capture images by camera 20.

As shown in FIG. 2C, a camera mount 109 is attached to side housing 16 of side wall 103*b*. Camera mount 109 is adapted to receive and position camera 20 relative to fixed datum 107 for viewing of sample 106 within cavity 44 by camera 20. While camera 20 is capable of capturing photographic images (i.e., reflection based images) of sample 106, it is also sensitive enough to capture luminescence images thereof. Camera 20 may employ a charge coupled device (CCD), a photodiode array, a photogate array, or similar image capture device.

A moveable stage apparatus 200 is disposed in interior cavity 44, and includes a transport mechanism 202 and a stage 204 to support the light-emitting sample 106. Moveable stage apparatus 200 is capable of two degrees of freedom movement to reposition the stage 204 (and sample 106) to a plurality of positions within interior cavity 44. Any one position therebetween may be retained for image capture.

As shown in FIGS. 2A-C, the transport mechanism 202 in the embodiment comprises two linear actuators 206 and 208 oriented at substantially perpendicular to one another. Each linear actuator 206 and 208 is capable of positioning stage 204 linearly along the respective actuator. Linear actuator 206 provides vertical positioning for stage 204 while linear actuator 208 provides horizontal positioning for stage 204. Linear actuator 206 has a stationary portion attached to box 12 and a mobile portion attached to linear actuator 208. Linear actuator 208 has a relatively stationary portion attached to linear actuator 206 and a mobile portion attached to stage 204. An example of one such linear actuator suitable for use in the transport mechanism 202 is a LC-33 produced by Thomson Industries of Port Washington, N.Y. Each linear actuator 206 and 208 also includes displacement limiting devices on either end to restrict motion along their respective mobile portions.

The transport mechanism 202 preferably includes a set of position sensors that are operably coupled to the computer 28 to provide position feedback to control the position of stage 204. In this case, the position sensors include a string or thin string 144 having one end attached to the stage 204 while the other end is attached to a take-up reel 212*a* (FIG. 2A). Based on the amount of string 144 wound on the reel and the total length of the string 144, computer 28 can determine the length of string between the stage 204 and the sensor 142, (i.e., based on changing resistance of the string with length and by using a look-up table in computer 28 to carry out the conversion). In another embodiment, the position sensor is provided by a laser positioned in interior cavity 44 to intercept the moveable stage 204 at a starting vertical or horizontal position. The laser may then be used to calibrate the position of the moveable stage 58 to a common vertical or horizontal position.

Linear actuators 206 and 208, position sensors 212, and computer 28 combine to provide closed loop position control for stage 204 within interior cavity 44. More specifically, a user, via computer 28, may input one or more positions for stage 204 along a substantially circular path about fixed datum 107. In one embodiment, a user provides a viewing angle for stage 204 relative to fixed datum 107. Software included in computer 28 then converts the viewing angle into control signals for moving each of the linear actuators 206 and 208. Motors included in each of the two linear actuators 206 and 208 then receive the control signals provided by computer 28 and position stage 204 accordingly. The motion of stage 204 between image capture positions may be accomplished by simultaneous motion of actuators 206 and 208 or by stepwise sequential activation of each of the actuators 206 and 208.

Light transmission device 111, as best reviewed in FIGS. 2A-2C, directs light reflected or emitted from sample 106 along the direction of fixed datum 107 and into lens 100 for image capture by camera 20. Light transmission device 111 is mounted to housing 16 using stationary bracket 119 (FIG. 2A), which includes circumferentially disposed bearings between stationary bracket 119 and moving bracket 126 that allow mirror assembly 120 to rotate freely relative to stationary bracket 119. Mirror assembly 120 is thus rotably coupled to housing 16 and rotates about an axis co-axially aligned with the stationary axis of the fixed datum 107.

Referring to FIG. 2C, mirror assembly 120 comprises an angled mirror 121 that reflects light from sample 106 on stage 204 in a direction along fixed datum 107. Outer wall 123 is substantially cylindrical and includes aperture 122 that enables light to pass between stage 204 and mirror 121. Outer wall 123 of mirror assembly 120 also prevents residual light in interior cavity 44 not directly associated with the current viewing angle of stage 204 from reaching lens 100. This is partially performed by configuring mirror 121 to be sufficiently long to span the length of stage 204. As the stage is positioned along the circular path about the stationary axis, outer wall 123 and mirror 121 cooperate to collect light primarily from the angular direction of stage 204 which is then reflected along fixed datum 107 for reception by lens 100.

Figure 2F:
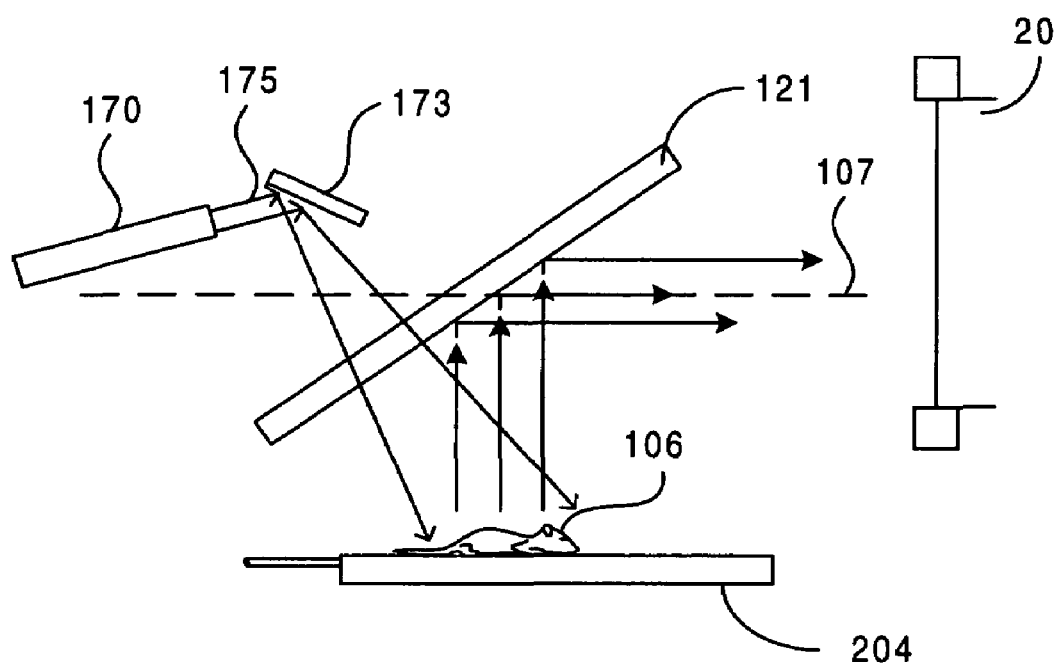
FIG. 2F illustrates a simplified view of light transmission within box using the light transmission device included in box of FIG. 1A.

FIG. 2F illustrates a simplified view of light transmission within box 12 using light transmission device 111. As shown in FIG. 2F, for the position of stage 204 as shown in FIG. 2A, light is emitted from sample 106, reflected off mirror 121, and transmitted along fixed datum 107.

In one embodiment, a light source is provided within the barrel of mirror assembly 120 to illuminate the sample or specimen in the imaging box 12. The light source may be continuously illuminated or flashed to capture photographic images of the sample and is turned off when capturing luminescence images. In a specific embodiment, the light source comprises a ring of low-wattage lights disposed circumferentially around the camera lens 100. In another embodiment, the light source comprises four pairs of white-light emitting diodes (LEDs), one pair mounted in each of four corners around the camera lens 100. One advantage of using LEDs is that the spectral emission thereof may be contained to visible light while excluding infrared light. Wires (not shown) may extend from the lights to the electronic components 56 and computer 28 to allow light levels to be controlled externally through the computer 28.

FIG. 2F also illustrates the use of structured light source 170. As shown, structured light 175, emitted from structured light source 170, reflects off a mirror 173, passes through partially transparent mirror 121, and onto sample 106. In one embodiment, the partial transparence of mirror 121 is achieved using a half-silvered or partially silvered mirror. In another embodiment, a dichroic mirror having wavelength specific transparency properties is used. The structured light 175 may then be captured by camera 20.

In the embodiment shown in FIGS. 2A-2E, light transmission device 111 employs computer 28 to control and position mirror assembly 120 relative to fixed datum 107. Mirror assembly 120 includes circumferentially disposed teeth on the inside of moving bracket 126 (teeth not shown) that engage a belt driven by a mirror assembly motor 128 (FIG. 2E). Moving bracket 126 then provides rotational motion relative to stationary bracket 119 for motor 128 input. Motor 128 is in electrical communication with the electrical components 56 and controlled by computer 28. Together, motor 128 and a processor in computer 28 cooperated to control the rotary position of mirror assembly 120.

The two degrees of freedom movement provided by transport mechanism 202 allow stage 204 and sample 106 to be positioned at multiple angles relative to fixed datum 107 for image capture by camera 20. Thus, based on user input via computer 28, transport mechanism 202 and light transmission device 111 cooperate to direct light from sample 106 on stage 204 to fixed datum 107 and lens 100 to capture image using camera 20. In addition to providing full 360 degree angular viewing of sample 106 about the circular path, transport mechanism 202 is capable of varying the image depth for a given angle of stage 204 relative to fixed datum 107. Together, transport mechanism 202 and light transmission device 111 cooperate to provide a field of view for camera 20 in the range of about 7.5 cm to about 16.5 cm. In a specific embodiment, light transmission device 111 cooperate to provide a field of view for camera 20 in the range of about 13 cm to about 16.5 cm. Similar to the user initiated angular position control described above, a user may input a desired focal depth and viewing angle for stage 204. Software included in computer 28 and linear actuators 206 and 208 would then combine to position stage 204 at the desired angle and depth relative to fixed datum 107.

To prevent undesirable contact between stage 204 and mirror assembly 120 during operation, transport mechanism 202 may incorporate crash protection measures. In one embodiment, the crash protection measures are software based and controlled by a processor in computer 28. Thus, based on position feedback of stage 204 and known position of mirror assembly 120, computer 28 generates control signals that insure that stage 204 does not undesirably contact with mirror assembly 120. This may be advantageous for movement of stage 204 between a position such as that shown in FIG. 2C and a position 180 degrees away. In this case, the processor of computer 28 transmits control signals to linear actuators 206 and 208 which move stage 204 orbitally around mirror assembly 120, e.g., by maintaining a minimum radius from fixed datum 107.

Figure 3A:
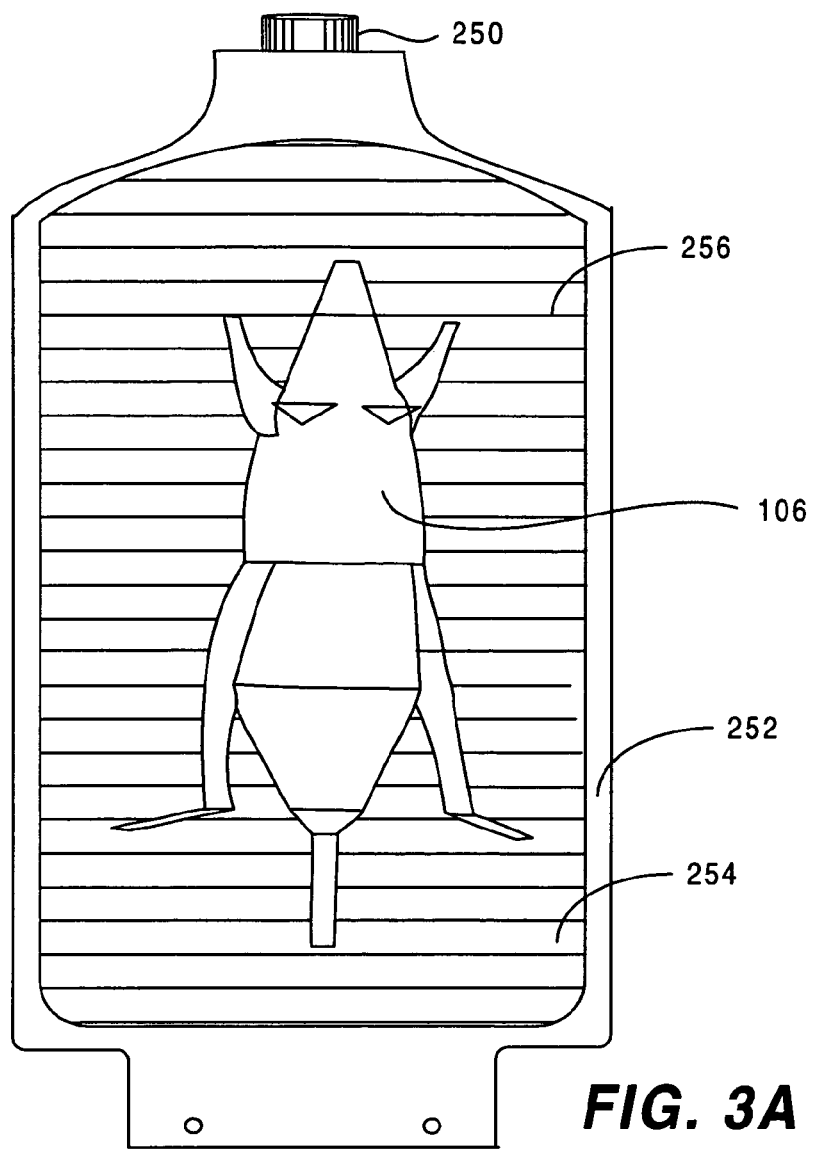
FIGS. 3A and 3B illustrate a top and side view, respectively, of the stage included in the imaging box of FIG. 1A in accordance with one embodiment of the present invention.
Figure 3B:
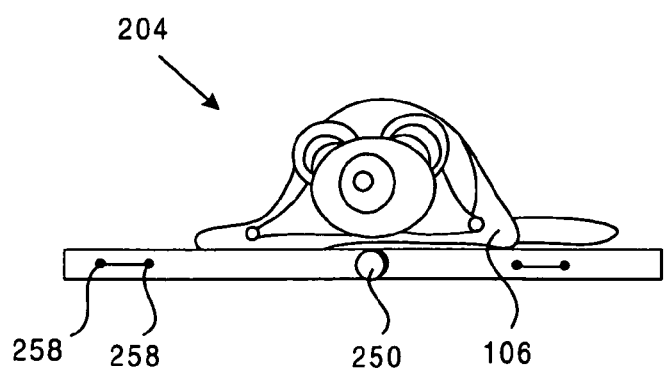

Referring now to FIGS. 3A and 3B, a top and side view, respectively, of stage 204 is illustrated in accordance with one embodiment of the present invention.

In one embodiment, stage 204 includes hardware based crash protection measures that prevent undesirable contact between stage 204 and other components within box 12. In a specific embodiment, crash pin 250 is placed on the side of stage 204 closest to the camera 20, as shown in FIG. 3A. Crash pin 250 prevents contact between stage 204 and components within cavity 44. To prevent contact between stage 204 and light transmission device 111, camera 20 or wall 103*b*, a metal ring 260 is perimetrically disposed around light transmission device 111 on stationary bracket 119. Since metal crash pin 250 is ground and metal ring 260 is maintained at 5V, inadvertent contact between crash pin 250 and metal ring 260 acts as a limit switch and provides immediate electrical communication with computer 28 that contact has been made with stage 204. Movement of stage 204 is then stopped. Together, crash pin 250 and metal ring 260 provide a circular crash protection boundary around light transmission device 111 during movement of linear actuators 206 and 208.

In another embodiment, software based crash protection may be implemented for preventing undesirable stage 204 contact with components within cavity 44. Based on position feedback of stage 204 using position sensors 212 and known position of mirror assembly 120, computer 28 provides control signals that ensure stage 204 does not overlap with mirror assembly 120, thus minimizing the risk of undesirable contact between sample 106 and components within cavity 44.

As shown in FIG. 3A, stage 204 comprises a frame 252 and a transparent portion 254. Transparent portion 254 allows light emitted or reflected from sample 106 to be transmitted to light transmission device 111 with substantially no interference and minimal distortion for any position of stage 204 about fixed datum 107. Transparent portion 254 preferably, comprises a transparent wire array 256 that supports sample 106. In a specific embodiment, transparent wire array 256 is a single transparent nylon line interwoven through holes 258 on opposing edges of frame 252 and secured in a taut manner to support sample 106. In another embodiment, array 256 is a mesh that resembles a cross pattern grid similar to a tennis racket mesh.

Box 12 may also include other components to facilitate image capture of a sample within box 12. In addition to automated focus control of the camera lens 100, the system 10 also includes an automated filter select device 117 capable of selectively providing multiple filters 118 at least partially between the camera 20 and light passing along fixed datum 107. The filters 118 may each facilitate image capture for one or more particular imaging applications. As shown in FIG. 2D, the optical filter select device 117 includes a circular filter select wheel 116 adapted to carry a plurality of optical filters 118 around its perimeter. The wheel 116 is rotatably mounted at its center to a mounting bracket 130 attached to side housing 16. The filter wheel 116 is mounted off-center from lens 100 such that the individual filters 118 can each be rotated into position to intersect light emitted from the sample and reflected by mirror 121 before reaching the camera lens 100. Filter wheel 116 has a groove along its perimeter edge in which a toothed belt 131 is seated. The toothed belt 131 is also engaged with a drive wheel 134 on a filter wheel motor 136. The filter wheel motor 136 is in electrical communication with the electrical components 56 and controlled by a processor included in computer 28. The plurality of optical filters 118 carried by filter wheel 116 may include any of a variety of optical filters for facilitating image capture such as a neutral density filter for bright samples, one or more wavelength cutoff filters for restricting specific wavelengths, a fluorescent filter for fluorescence applications in which the excitation light differs from the detected light, etc.

Other components used to facilitate image capture of a sample within box 12 may also include a gas manifold to anesthetize one or more mammalian samples. In one embodiment, the gas manifold is detachably coupled to stage 204 and includes a plurality of interfaces. Each interface is adapted to provide a gas to a mammalian sample resting on the stage 204. An exemplary gas manifold suitable for use with the present invention is described in commonly owned co-pending U.S. Pat. No. 09/795,056 by Nelson et al. filed on Feb. 21, 2001, the entire disclosure of which is incorporated herein by reference for all purposes.

Figure 3C:
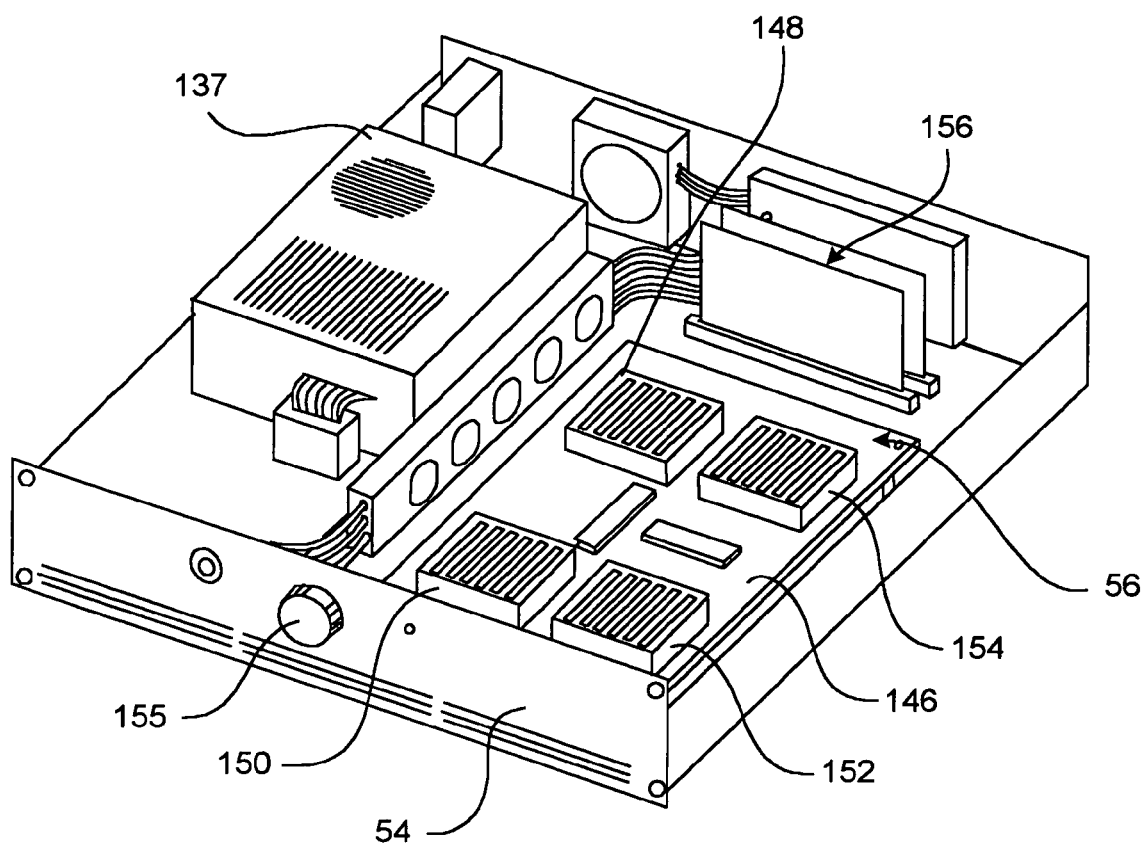
FIG. 3C illustrates a top perspective view of drawer and electronic components housed therein in accordance with one embodiment of the present invention.

Referring now to FIG. 3C, there is shown a top perspective view of drawer 54 and electronic components 56 housed therein. As previously noted, these components interface with computer 28 and are used to control the various motors and other components of imaging system 10. A 3 V power supply 137 provides electrical power to the various active components in the drawer 54. A motor control board 146 has four motor controllers 148, 150, 152, 154 mounted thereon. The motor controllers 148, 150, 152, 154 are in communication with each of the F-stop motor 109, lens focus motor 114, filter wheel motor 136, mirror assembly motor 128, and stage motor 138, respectively. Suitable control boards include the TMG control board as provided by TMG of Mountain View, Calif. Each motor controller interfaces, via cable 34, with computer 28 where the motor controllers and motors are controlled by user input and appropriate software running on computer 28. Drawer 54 also houses a data acquisition board (DAB) 156. On the face of drawer 54 is a knob 155 which is in communication with an interior cavity 44 light source and allows a user to manually to control the light intensity in the interior cavity 44.

The F-stop motor 109, lens focus motor 114, mirror assembly motor 128, and filter wheel motor 136 are each stepper motors capable of suitable position control of their respective components. By way of example, a model number SST 39D 1010 (1.8 deg/step, 4.3V, 0.85 A), manufactured by Shinano Kenshi Co., Ltd, Japan, is suitable for use with any of the motors 109, 114, 128 and 136. Each of the motors is in electrical communication with one or more electronic components 56 housed in drawer 54. The electronic components 56 are, in turn, in communication with the computer 28 where the motors 109, 114, 128 and 136 may be controlled by appropriate software and/or by user input.

Figure 4A:
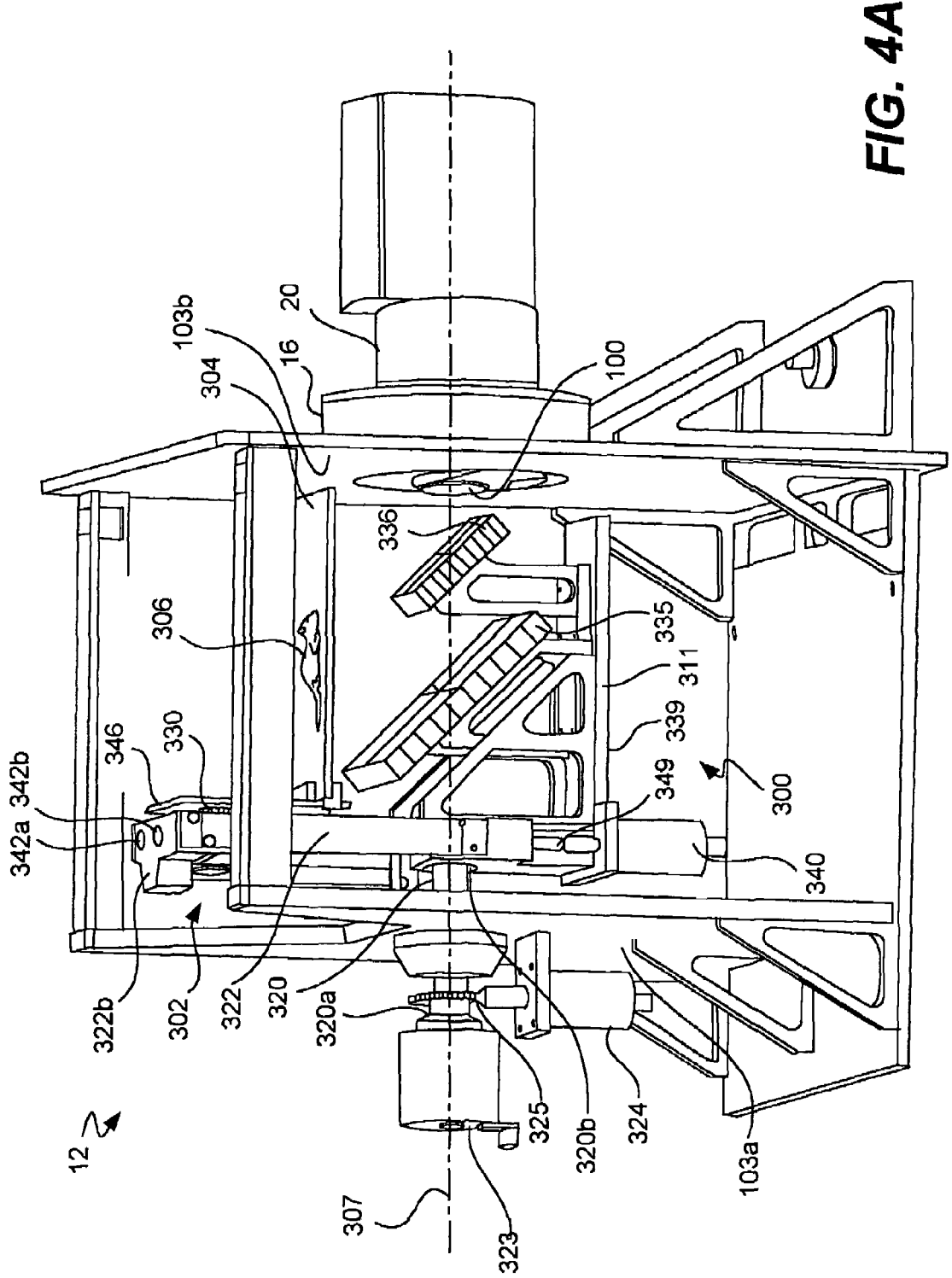
FIG. 4A illustrates a top perspective view of the components in the box of FIG. 1A with the exterior walls removed showing the moveable stage directly below a fixed datum in accordance with another embodiment of the present invention.
Figure 4B:
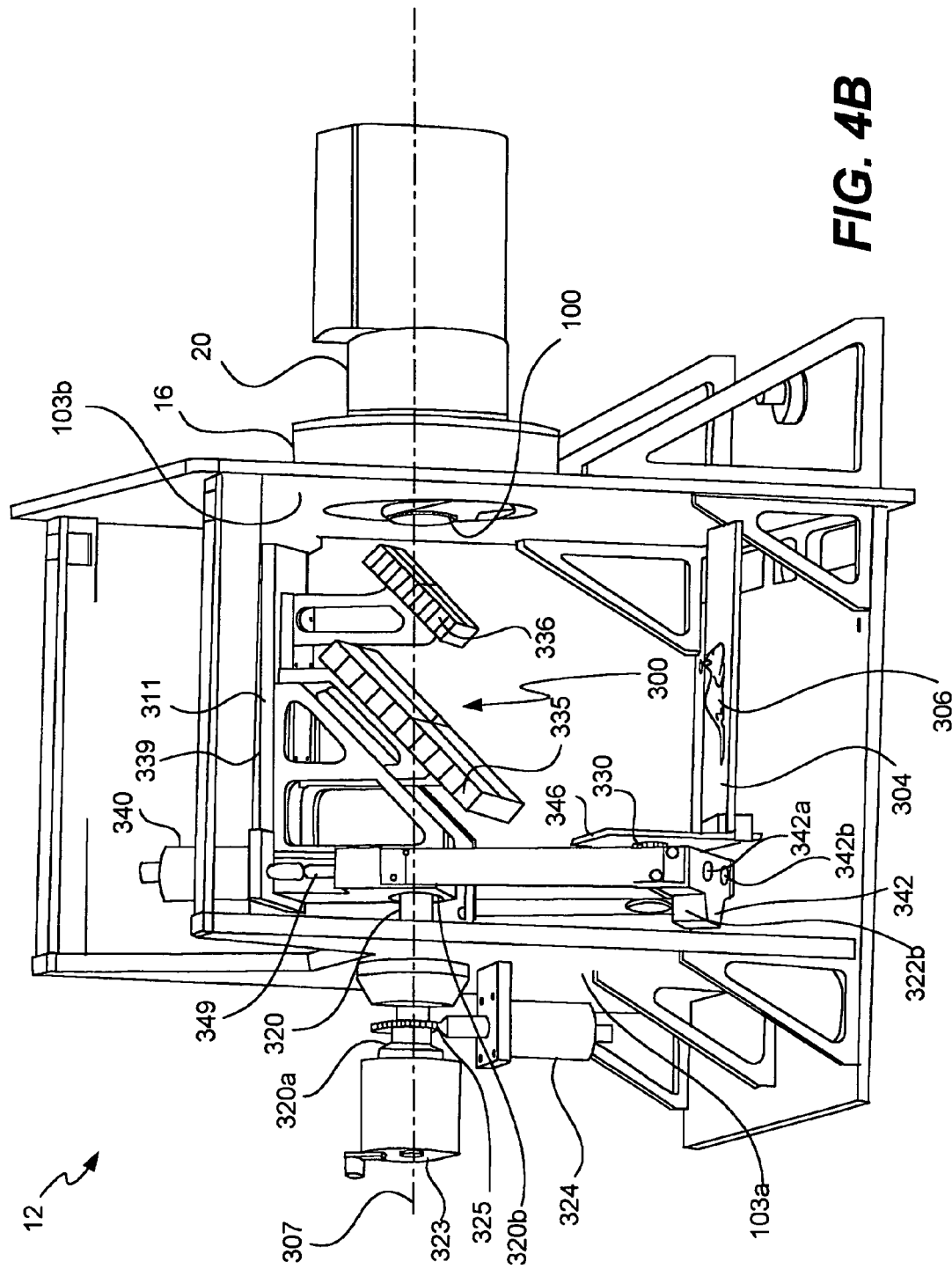
FIG. 4B illustrates a top perspective view of the components in the box of FIG. 1A with the exterior walls removed showing the moveable stage below and off-center from the fixed datum in accordance with another embodiment of the present invention.
Figure 4C:
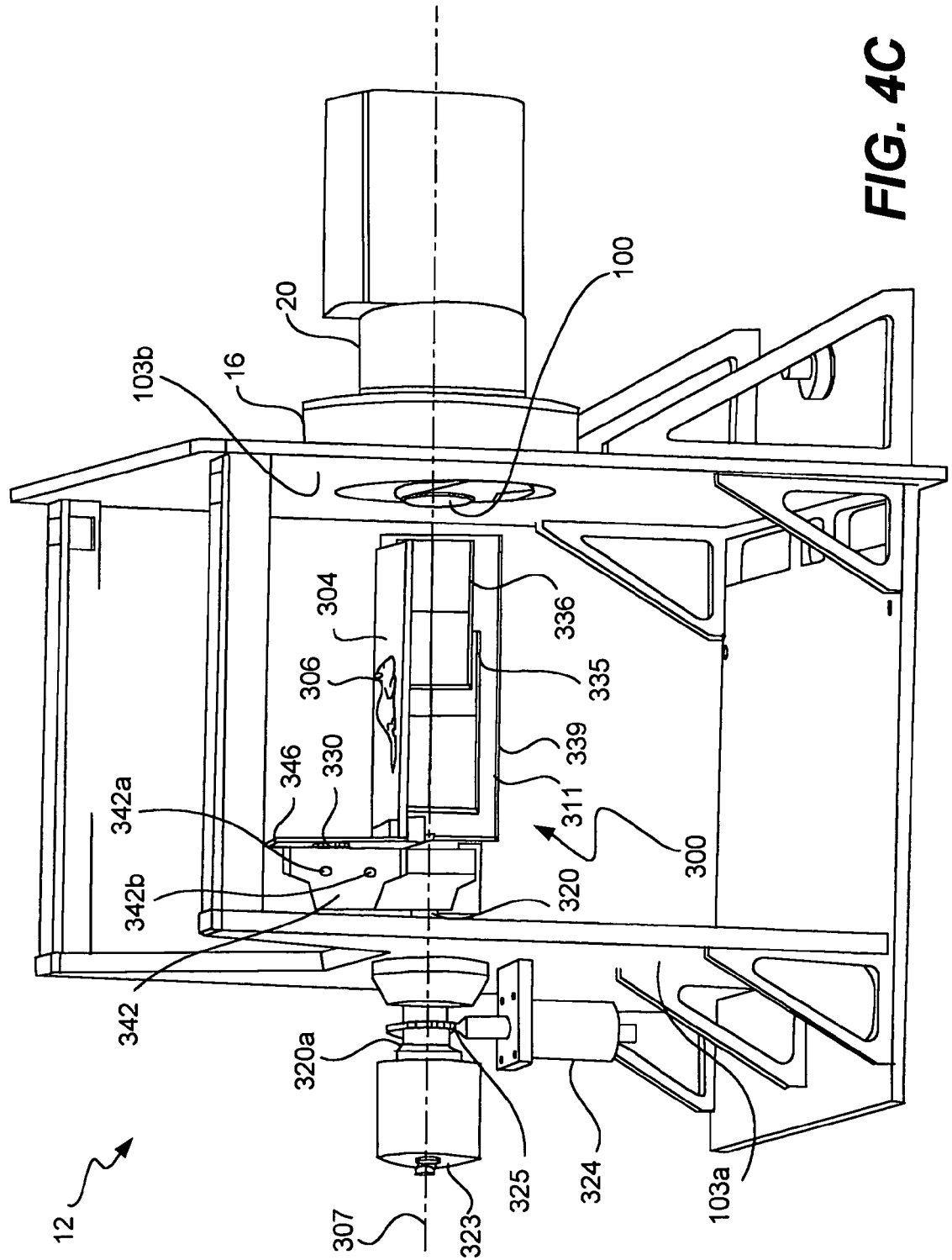
FIG. 4C illustrates a top perspective view of the components in the box of FIG. 1A with the exterior walls removed showing the moveable stage above and off center from the fixed datum in accordance with another embodiment of the present invention.

Referring now primarily to FIGS. 4A-C, an imaging apparatus for capturing an image of sample 306 with camera 20 is illustrated in accordance with another embodiment of the present invention. FIG. 4A is a top perspective view of the components in box 12 with the exterior walls removed showing stage 304 directly above fixed datum 307. FIG. 4B is a top perspective view of the components in box 12 with the exterior walls removed showing stage 304 below and off-center from fixed datum 307. FIG. 4C illustrates a top perspective view of the components in box 12 with the exterior walls removed showing the moveable stage above and off center from fixed datum 307.

Box 12 includes a camera lens 100 mounted on side housing 16 and coupled to camera 20, similar to that as described with respect to FIGS. 2C-2E. This datum 107, for clarity, is represented by a stationary axis that provides a reference line of site upon which the transport mechanism 202 and the light transmission device 111 cooperate therebetween to direct light reflected or emitted from sample 106 towards and into the camera lens 100 to capture images by camera 20.

A moveable stage apparatus 300 is disposed in interior cavity 44, and includes a transport mechanism 302 and a stage 304 to support the light-emitting sample 306. Moveable stage apparatus 300 is capable of two degrees of freedom movement to reposition the stage 304 (and sample 306) to a plurality of positions within interior cavity 44. Any one position therebetween may be retained for image capture.

As shown in FIGS. 4A-C, transport mechanism 302 rotates about main axis 320 which passes through side wall 103a. The center of rotation for main axis 320 which is co-axially aligned with the stationary axis of fixed datum 307. Bearings are included between main axis 320 and sidewall 103a which allow main axis 320 to rotate freely relative to side wall 103a. A proximal end 320a of main axis 320 is fixed to worm gear 325, which is operably driven by motor 324. A distal end 320b of main axis 320 is fixed to a positioning arm 322 which supports the moveable stage apparatus 300. As motor 324 rotates worm gear 325, this rotational motion is transmitted to the positioning arm 322 and the movable stage apparatus 300 for rotation about fixed datum 307. A S23T as provided by Industrial Devices Corp. of Petaluma, Calif. is suitable for use as motor 324.

Motor 324 is in electrical communication with electrical components 56 and controlled by computer 28. Together, the motor 324 and the processor in computer 28 position movable stage apparatus 300 along the circular path about fixed datum 307. An electrical slip ring 323 is provided to electrically couple the components of box 12 to the stage mechanism to maintain continuous electrical communication regardless of the rotation of positioning of main axis 320 without risk of wrapping. A AC4831-18 as provided by Industrial Devices Corp. of Petaluma, Calif. is suitable for use as electrical slip ring 323.

Figure 4D:
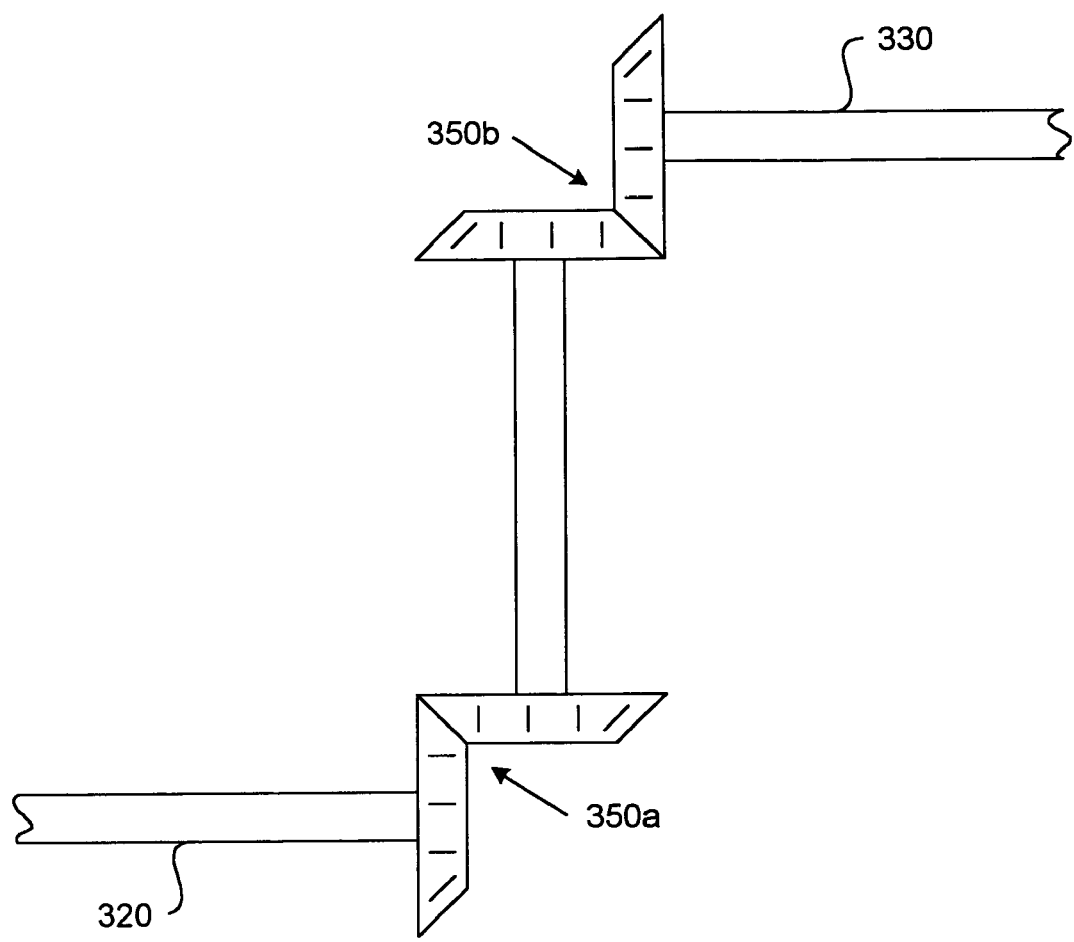
FIG. 4D illustrates a gearing mechanism used to maintain the horizontal position of the moveable stage of FIG. 4A in accordance with another embodiment of the present invention.

Positioning arm 322 provides the main structural support for movable stage apparatus 300 upon which stage 304 is rotably and slideably coupled. Stage 304 is coupled to positioning arm 322 in a manner such that, as positioning arm 322 rotates via main axis 320 about fixed datum 307, stage 304 remains substantially horizontal relative the bottom of cavity 44. This allows a sample 306, which is supported atop stage 304, to be viewed from multiple positions and angles without falling off stage 304. To maintain the stage 304 in this horizontal position as the positioning arm 322 rotates about main axis 320, a set of bevel gears 350a and 350b are disposed between main axis 320 and a rod 330 that rotably couples stage 304 to main support 322 (FIG. 4D). The bevel gears 350a and 350b thus rotably couple main axis 320 to stage 304. The bevel gears 350a and 350b reverse rotation received by rod 330 for rotation provided by main axis 320 in a 1:1 reverse gear ratio. For example, as main axis 320 rotates clockwise 30 degrees, rod 330 rotates counterclockwise 30 degrees via bevel gears 350a and 350b, thus keeping stage 304 horizontal. In this manner, stage 304 remains substantially horizontal for any rotation position of positioning arm 322 relative to box 12, as shown in FIGS. 4B and 4C.

Centrally attached to main support 322 is light transmission device 311. Light transmission device 311 rotates with main support 322 about fixed datum 307 and directs light reflected or emitted from sample 106 along fixed datum 307 and towards lens 100 for image capture by camera 20. Light transmission device 311 includes two mirrors 335 and 336. Each mirror 335 and 336 is attached to mirror support 339, which is fixed to and extends perpendicularly from positioning arm 322. Mirrors 335 and 336 rotate with positioning arm 322 about fixed datum 307. Each mirror 335 and 336 is configured to reflect light emitted or reflected from sample 306 at least partially along fixed datum 307 and towards lens 100.

Rotation about main axis 320 using motor 324 provides a first rotational degree freedom for movable stage apparatus 300. Movable stage apparatus 300 also includes a second degree of freedom. More specifically, stage 304 may translate linearly along positioning arm 322 towards and away from mirrors 335 and 336 to vary the field of view for viewing of sample 306 on stage 304. To allow linear translation of stage 304 along positioning arm 322, positioning arm 322 includes a linear slide 342 which includes two cylindrical holes for receiving slide bars 342a and 342b therethrough. Sliding mount 346 allows attachment by stage 304 to linear slide 342. Sliding mount 346 is rotably coupled to linear slide 342 via rod 330 and bearings disposed therebetween. Thus, stage 304 is orthogonally fixed to sliding mount 346, which rotates via rod 330 and translates via linear slide 342.

Motor 340 is capable of moving sliding mount 346 along slide bars 342a and 342b using a worm gear 349 operably coupled to motor 340 and linear slide 342. A SSD55D5C0D0 as provided by Shinano Kenski Co. of Japan is suitable for use as motor 340. Together, motor 340 and a processor in computer 28 act to position stage 304 relative to mirrors 335 and 336 to control the field of view for viewing of sample 306 on stage 304.

In operation, movable stage apparatus 300 and light transmission device 311 may be used as follows. A user, via computer 28, inputs one or more positions or angles for stage 304 relative to fixed datum 307. For example, the user may provide two viewing angles for stage 304 relative to fixed datum 307, both having the same field of view. For the first viewing angle, software included in computer 28 then converts the viewing angle into control signals for controlling motor 324. Motor 324 then receives the control signals provided by computer 28 and positions stage 304 at the first position having a first angle relative to fixed axis 307. After imaging is complete from the first viewing angle, software included in computer 28 then sends control signals to motor 324, which re-positions stage 304 at the second position having a second angle relative to fixed axis 307.

Each mirror 335 and 336 is designed to provide a different field of view for imaging within cavity 44. Coupled with the ability to move stage 304 towards and away from mirrors 335 and 336, mirror 335 provides a field a view in the range of about 15 cm to 25 cm. Similarly, mirror 336 a field a view in the range of about 9 cm to 11 cm.

Similar to the stage embodiment in FIG. 3A, stage 304 comprises a transparent portion that allows light emitted or reflected from sample 306 to be transmitted to light transmission device 311 with substantially no interference and minimal distortion for any position of stage 304 about fixed datum 307. In addition, movable stage apparatus 300 includes hardware based crash protection devices that prevent undesirable contact between stage 304 and other components within box 12. For example, slide 342 includes a hard stop at each end to prevent movement of stage 304 to undesirable positions along positioning arm 322. Further, main axis 320 also includes a hard stop at the top center thereof that prevents movable stage apparatus 300 from continually circling about main axis 320. Upon reaching the hard stop at top center from a first direction, movement to the other side of the hard stop at top center may be accomplished by rotating the movable stage apparatus about main axis 320 360 degrees in the opposite direction.

III. Operation of the Imaging System

The present invention may be employed in a wide variety of imaging applications. Generally, the present invention may be applied with any non-invasive methods and compositions for detecting, localizing and tracking light-emitting entities and biological events in a mammalian subject. For example, the imaging system 10 may be implemented with intensified Charge-Coupled Device (CCD) cameras to detect the localization of light-producing cells (e.g., certain bacteria or tumor cells made bioluminescent by transforming them with luciferase DNA constructs) inside of living animals, such as mice. In such applications, an animal containing the bioluminescent cells is placed inside of box 12 and on stage 204. Camera 20 is then activated to detect the emitted photons. The photon signal may then be used to construct a luminescent image of photon emission. The luminescent image is constructed without using light sources other than the luminescence from the sample itself. This luminescence is recorded as a function of position to produce the luminescence image. The photographic image may also be taken of the same sample to aid in position visualization of the luminescent image. One approach to generating such composite photographic/luminescence images is described in U.S. Pat. No. 5,650,135 issued to Contag et al. on Jul. 22, 1997. The entire disclosure of that patent was previously incorporated herein by reference.

Turning now to FIG. 5, process flow 500 illustrates a method of capturing photographic and luminescent images using the imaging system 10 in accordance with one embodiment of the present invention. Process flow 500 begins by placing a specimen or assay to be imaged for light emission on stage 204 within imaging box 12 (202). Using computer 28, a user inputs a desired position for stage 204. Based on the input, transport mechanism 202 moves stage 204 to the corresponding position according to a control signal provided by computer 28 (504). Light transmission device 111 also re-positions according to a control signal provided by computer 28. The imaging box 12 and associated image components are then prepared for photographic image capture of the sample (506). Preparation may include launching imaging and acquisition software (e.g., "LivingImage" as provided by Xenogen Corporation of Alameda, Calif.) on the computer 28 and initializing camera 20. Further preparations may include closing door 18, activating the photographic capture option in the software, focusing camera 20 to a specific depth of the sample or animal, and turning on the lights in box 12. Preparations may also include focusing lens 100, selectively positioning an appropriate lens filter 118, setting the f-stop, etc.

A photographic image is then captured (508). In one embodiment, a "live mode" is used during photographic imaging of the sample to observe the sample in real time. The live mode includes a sequence of photographic images taken frequently enough to simulate live video. Upon completion of photographic capture, the photographic image data is transferred to an image processing unit 26 and/or a processor in computer system 28 (510). These may be used to manipulate and store the photographic image data as well as process the data for display on computer monitor 38.

Subsequently, with stage 204 at the same position, the imaging apparatus 10 is prepared for luminescence image capture (512). Such preparation may include selecting luminescent exposure time and binning level using the computer 28, and turning off the lights in interior cavity 44. When ready, the CCD camera 20 then captures (514) the luminescence image over a set period of time (up to several minutes). The luminescence image data are transferred to the image processing unit 26 and/or a processor in computer 28 (516).

At this point, a user may manipulate and store the luminescence image data as well as process it for display on the computer display 38. The manipulation may also include overlaying the luminescent image with the photographic image and displaying the two images together as a 2-D "overlay" image, with the luminescence data typically shown in pseudocolor to show intensity. This overlay image may then be the basis for user analysis and may be analyzed and manipulated as desired. In particular, an analysis may include a summation of the illumination magnitudes over the pixels within a portion of the luminescence representation. Note that although the discussion will focus on a single luminescence representation for the overlay image, the process flow 500 may include taking multiple luminescence representations from the same position of stage 204, e.g., at the same time or a later time (518).

If desired, stage 204 may then be moved to a second position (520). While the stage is at the second position, one or more photographic and/or luminescence images of the sample may be captured as described above. Upon completion of each image capture, a processor in computer 28 then receives the image data. Image collection may further continue by capturing images of the sample from alternate positions and views of the sample.

As mentioned, the photon emission data may represent the specific pixels on the CCD camera 20 that detect photons over the duration of the image capture period. Together, a structured light photographic representation of the sample and a luminescence representation of the sample may be combined to form a structured light superposition or overlay image. Because the imaging apparatus 100 is typically used to measure the entire sample 106, the data in the luminescence representation typically has one or more distinct luminescent portions of interest.

In one embodiment, the present invention includes the use of structured light during image capture. In this case, imaging apparatus 100 provides a sequence of images of a small animal containing a bioluminescent source. This sequence of images is taken at different viewing angles and provides the information necessary to reconstruct the location, brightness, and size of the bioluminescent source within the animal. Once the images are received by processor 28, one suitable reconstruction algorithm (or inversion algorithm) suitable for use with the present invention is diffuse optical tomography. In order to apply diffuse optical tomography, it is necessary to determine the 3D surface topology of the animal and to map the bioluminescent emission onto this surface. In one embodiment, 3D surface topology is accomplished using a structured light projection system.

Structured light uses a series of lines of light that are projected down on an object at an angle (at about 30 degrees, for example) to the surface normal. The lines bend as they pass over the object, and the bend in the lines can be used to determine the height of the surface at all locations that are illuminated by a structured light projector 170. As shown in FIG. 2A, structured light projector 170 is attached to and rotates with light transmission device 11. In this case, structured light projector 170 consists of a Kohler illumination system where a slide is illuminated by a light source and then an image of the slide is projected onto the animal. The projection angle is large enough to get sufficient "bend" in the lines to achieve spatial resolution, but small enough that large shadows are not present.

An image of the structured light is taken with camera 20. After the 2-D structured light images have been captured and stored, computer 28 may then process the structured light data to generate a structured light representation (522). As one of skill in the art will appreciate, there are numerous conventional algorithms for reconstructing a surface from structured light images. For example, the phase shift of each line at all points on the image can be determined from a computationally-efficient 2D Fourier transform. The actual surface height is then computed by "unwrapping" the phase map.

Each structured light image provides the surface topology for approximately the facing half of the animal only. By taking images from several viewing angles, e.g., about every 45 degrees, the entire 3D surface of the animal can be reconstructed by "stitching" together the partial surface reconstructions obtained from each view.

Although the present invention has been discussed primarily in the context of a moveable stage useful for in-vivo imaging applications, the present invention is suitable for other imaging applications and may be tailored correspondingly. In addition, although the present invention has been described with respect to an isolated box 12 and separate computer 28, one embodiment of the present invention relates to a stand-alone cabinet unit housing all imaging components and computer processing components therein. Further, the present invention is scalable and may be adapted in size to fit to needs of a particular application. Although various details have been omitted for brevity's sake, obvious design alternatives may be implemented. Therefore, the present examples are to be considered as illustrative and not restrictive, and the invention is not to be limited to the details given herein, but may be modified within the scope of the appended claims.

What is claimed is:

1. A method for imaging a sample, the sample supported by a stage moveable within an imaging box, the imaging box coupled to a camera configured to capture an image of the sample, the method including:
    moving the stage to a first position in the imaging box;
    capturing a first image of the sample from the first position using the camera;
    moving the stage to a second position in the imaging box, wherein the second position has a different angle relative to a fixed datum associated with the camera than the first position;
    capturing a second image of the sample from the second position using the camera;
    directing light, using a light transmission device, reflected or emitted from the sample to the fixed datum to capture the image by the camera; and
    rotating the light transmission device about the fixed datum when the stage moves from the first position to the second position.

2. The method of claim 1 wherein the light transmission device comprises a minor that reflects light emitted from the sample towards the fixed datum.

3. The method of claim 1 wherein the fixed datum includes a fixed axis that passes though a camera mount on a wall of the imaging box.

4. The method of claim 1 further including capturing a third image of the sample from the first position.

5. The method of claim 1 wherein the first image comprises luminescent light data and the third image comprises photographic data.

6. The method of claim 1 wherein the camera is fixed to a wall of the imaging box.

7. The method of claim 6 wherein the camera is fixed to a side wall or a vertical wall of the imaging box.

8. The method of claim 1 wherein a portion of the stage that supports the sample is transparent.

9. The method of claim 1 further including transmitting structured light onto the sample while the sample is in the first position or the second position.

10. A method for imaging a sample, the sample supported by a stage moveable within an imaging box, the imaging box coupled to a camera configured to capture an image of the sample, the method including:
    moving the stage to a first position in the imaging box;
    capturing a first image of the sample from the first position using the camera;

moving the stage to a second position in the imaging box, wherein the second position has a different angle relative to a fixed datum associated with the camera than the first position;

capturing a second image of the sample from the second position using the camera; and rotating, using a moveable stage apparatus that couples to the stage, the stage about the fixed datum.

11. The method of claim 10 wherein the stage remains substantially horizontal during rotation about the fixed datum by the moveable stage apparatus.

12. The method of claim 10 further including directing light, using a light transmission device, reflected or emitted from the sample to the fixed datum to capture the image by the camera.

13. The method of claim 12 wherein the light transmission device rotates with the stage about the fixed datum.

14. A method for imaging a sample in an imaging box to capture light-based images of the sample, the method including:

rotating one of a stage or a camera to a first position of the stage relative to the camera in the imaging box;

capturing a first image of the sample using the camera;

rotating one of the stage or the camera to a second position of the stage relative to the camera in the imaging box, wherein the second position has a different angle of the stage relative to the camera than the first position;

capturing a second image of the sample using the camera; and rotating the light transmission device about the camera or the stage.

15. The method of claim 14 further including, using a light transmission device, directing light reflected or emitted from the sample to the camera while the stage is at the first position of the stage relative to the camera.

16. The method of claim 15 further including, using the light transmission device, directing light reflected or emitted from the sample to the camera at the second position of the stage relative to the camera.

17. The method of claim 15 wherein the light transmission device comprises a minor that reflects light emitted from the sample towards the camera.

18. The method of claim 14 wherein the camera is fixed to a wall of the imaging box.

19. The method of claim 14 wherein a portion of the stage that supports the sample is transparent.

20. The method of claim 14 wherein the stage is rotated from the first position to the second position and the camera remains fixed.

21. A method for imaging a sample in an imaging box to capture light-based images of the sample, the method including:

moving one of a stage or a camera to a first position of the stage relative to the camera in the imaging box;

rotating a light transmission device to direct light reflected or emitted from the sample to the camera while the stage is at the first position of the stage relative to the camera, wherein the light transmission device comprises a minor that reflects light emitted from the sample towards the camera;

capturing a first image of the sample using the camera;

moving one of the stage or the camera to a second position of the stage relative to the camera in the imaging box, wherein the second position has a different angle of the stage relative to the camera than the first position;

rotating the light transmission device to direct light reflected or emitted from the sample to the camera at the second position of the stage relative to the camera; and capturing a second image of the sample using the camera.

22. The method of claim 21 wherein a portion of the stage that supports the sample is transparent.

\* \* \* \* \*

UNITED STATES PATENT AND TRADEMARK OFFICE
CERTIFICATE OF CORRECTION

PATENT NO. : 7,589,786 B2  Page 1 of 1
APPLICATION NO. : 11/486239
DATED : September 15, 2009
INVENTOR(S) : Nilson et al.

It is certified that error appears in the above-identified patent and that said Letters Patent is hereby corrected as shown below:

On the Title Page of the Patent insert:
--Related U.S. Application Data
(63) Divisional of application No. 09/905,668, filed July 13, 2001.--

In the Claims:
Col. 16, line 42, (claim 2), change "minor" to --mirror--.

Col. 18, line 6, (claim 17), change "minor" to --mirror--.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,589,786 B2
APPLICATION NO. : 11/486239
DATED : September 15, 2009
INVENTOR(S) : Nilson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 521 days.

Signed and Sealed this

Fourteenth Day of December, 2010

David J. Kappos
*Director of the United States Patent and Trademark Office*